(12) United States Patent
Schoen et al.

(10) Patent No.: US 6,511,812 B1
(45) Date of Patent: Jan. 28, 2003

(54) METHOD AND TEST KIT FOR USE IN IMPROVING IMMUNOASSAY SPECIFICITY

(75) Inventors: Robert C. Schoen, Grayslake, IL (US); Yuzo Inoue, Matsudo (JP); Toshinori Takei, Tokyo (JP); Satoshi Jomura, Noda (JP); Susan E. Sweeney, Mundelein, IL (US); Joseph S. Niedbalski, Gurnee, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 08/737,775

(22) PCT Filed: May 9, 1994

(86) PCT No.: PCT/US94/05152

§ 371 (c)(1),
(2), (4) Date: Nov. 12, 1996

(87) PCT Pub. No.: WO95/30902

PCT Pub. Date: Nov. 16, 1995

(51) Int. Cl.[7] .................................................. G01N 33/53

(52) U.S. Cl. ............................. 435/7.1; 435/5; 435/7.92; 435/15; 435/975; 436/518; 436/528; 436/531; 436/538

(58) Field of Search ............................ 435/5, 7.1, 7.92, 435/7.94, 7.95, 25, 28, 172.3, 962, 974, 975, 15; 436/518, 528, 531, 538

(56) References Cited

U.S. PATENT DOCUMENTS 5,124,255 A * 6/1992 Bolling et al. ............. 435/69.3
5,330,893 A * 7/1994 Gilbert et al. ................ 435/7.1

FOREIGN PATENT DOCUMENTS

EP     0388232     9/1990
WO     92/15881     * 9/1992

* cited by examiner

*Primary Examiner*—Jeffrey Stucker
(74) *Attorney, Agent, or Firm*—Dianne Casuto

(57) ABSTRACT

An improved method for detecting antibodies is disclosed. The method employs a recombinant denatured bacterial enzyme. The invention also relates to a test kit useful for performing an immunoassay which comprises a container containing a denatured recombinant bacterial enzyme.

10 Claims, No Drawings

METHOD AND TEST KIT FOR USE IN IMPROVING IMMUNOASSAY SPECIFICITY

BACKGROUND OF THE INVENTION

The invention relates generally to a method for improving the specificity of immunoassays, and more particularly, relates to a method for adding denatured and/or purified bacterial enzyme to a specimen diluent to increase the specificity of immunoassays which utilize recombinant antigens expressed as fusion proteins with a bacterial enzyme.

Historically, immunoassays have been known to be prone to false positive reactions. Viral lysates or recombinant protein preparations, which comprise the typical antigen solutions which are utilize on the solid support, also can contain other proteins. These other proteins can bind to the solid support, introducing the possibility of reactivity with antibodies in the patient's sample. Alternatively, a component in the patient's sample can bind to the solid support and interfere with the assay.

For example, McFarlane et al., *Lancet* (1990) 335:754–57, reported a high prevalence of antibody to hepatitis C virus (HCV) in patients with autoimmune chronic active hepatitis (AI-CAH). They suggested that the serum of AI-CAH patients may contain a component that gives false-positive results in the assay. McFarlane et al. surmised that the assay might have been non-specifically detecting IgG since they saw a correlation between IgG levels and OD values, or that factors contained in the patient sera were responsible for the results, such as an antibody against some other pathogen which cross-reacts with the antigen used in the assay, or a component which adheres to the solid phase and binds IgG. In addition, some false positive results are due to cross-reactivity between the patient sera and the fusion protein used to express the recombinant antigen utilized in the assay.

Since reactivity such as that described herein can be expected, assays can be designed to circumvent some of the problems generally associated with utilizing the recombinant protein. See, for example, P.C.T. Publication No. WO 92/13275, which corresponds to U.S. Ser. No. 08/059,868 (now U.S. Pat. No. 5,330,893, issued Jul. 19, 1994) which is incorporated herein by reference. In that publication, it is taught that the addition of superoxide dismutase to the specimen diluent is useful in increasing the specificity in assays which utilize recombinant proteins produced as fusion proteins with superoxide dismutase (SOD). One skilled in the art would be led, based on this teaching, to add such a bacterial enzyme to the specimen diluent in order to increase specificity in assays which utilize recombinant proteins.

Surprisingly, however, applicants have discovered that the mere addition of such a bacterial enzyme, even if expressed in the same bacterial host system, may not lead to increased specificity in all types of fusion proteins. Thus, it would be advantageous to provide a method and reagents which could increase the specificity in immunoassays when fusion proteins are utilized as the capture and/or indicator reagent in an assay.

SUMMARY OF THE INVENTION

The present invention provides an improved method for increasing specificity in immunoassays which comprises the steps of (a) mixing the specimen with a diluent comprising a denatured recombinant bacterial enzyme expressed as a fusion protein with said bacterial enzyme, and (b) contacting said diluted specimen with at least one recombinant antigen expressed as a fusion protein with said denatured bacterial enzyme. The recombinant denatured bacterial enzyme comprises a recombinant protein, and can be either CKS or SOD. Further, the concentration of said recombinant denatured bacterial enzyme is from about 0.001 g/L diluent to about 1.0 g/L diluent. More preferably, the concentration of said recombinant denatured bacterial enzyme is from about 0.01 g/L diluent to about 0.1 g/L diluent. Most preferred, the recombinant bacterial enzyme is at a concentration of about 100 μg/m. The method can detect numerous analytes, including antibody to hepatitis C virus (HCV) and antibody to human immunodeficiency virus (HW). Denaturation can be accomplished by a variety of methods, including heat and urea Further, purified, recombinant bacterial enzyme may be utilized The present invention also provides a diluent useful for detecting antibodies in a test sample when performing an assay which uses at least one recombinant antigen expressed as a fusion protein with a recombinant bacterial enzyme, which diluent comprises the recombinant bacterial enzyme which has been denature. The concentration of said denatured recombinant bacterial enzyme is about 100 μg/ml. Purified, recombinant bacterial enzyme may be utilized.

The present invention also provides a test kit for performing an immunoassay which comprises a container containing a denatured recombinant bacterial enzyme selected from the group consisting of CKS and SOD.

DETAILED OF THE INVENTION

The present invention provides an improvement to methods for detecting antibodies in a specimen from an individual wherein a recombinant antigen employed in the method is expressed as a fusion protein by a vector and wherein the recombinant antigen is encoded with a gene of a bacterial enzyme such as CKS or SOD. The improvement comprises the step of mixing the specimen with a diluent comprising denatured recombinant bacterial enzyme (such as, SOD or CKS), wherein said enzyme also may be purified by methods known in the art as discussed herein, including anion-exchange resins and cation-exchange resins.

The denaturation of proteins by heat or chemical means is known in assay diagnostics when preparing serum samples for certain types of assay procedures. Denaturation of proteins occurs when the tertiary bonds of proteins are broken, which results in partial or complete unfolding of the protein. Usually, however, care is taken not to denature the protein solutions used for assays, since such denaturation can change the properties of such proteins, adversely affecting the results of the assay. See, for example, N. W. Tietz, ed., *Fundamentals of Clinical Chemistry*, 2nd Edition, W. B. Saunders Company, Philadelphia (1976), page 270.

Although it is known to add the recombinant bacterial enzyme utilized in the fusion protein to the assay diluent in order to improve assay specificity, it heretofore has not been known that the mere addition of such bacterial enzyme to a diluent may not result in the desired effect of increasing assay specificity by reducing the amount of false positive reactions. A false positive result is defined herein as one in which a sample is repeatably reactive in an ELISA, EIA or PHA but is not confirmed by alternative methods for the presence of analyte antibodies. Alternative testing methods include synthetic peptide EIAs, antibody blocking procedures and recombinant immunoblot assays.

Applicants have observed that in certain instances, addition of recombinant or purified recombinant bacterial enzymes does not result in increased specificity in assays which employ recombinant proteins. Applicants have surprisingly discovered that denaturaion of the recombinant bacterial enzyme results in increased specificity in assays. Also, applicants have discovered that at times it may be advantageous to utilize a purified, denatued, recombinant bacterial enzyme in a specimen diluent to increase the specificity of the assay.

It has been discovered that it is especially advantageous to add denatured, recombinant bacterial enzyme to a diluent (hereinafter defined) to improve the detection of analyte by increasing assay specificity. Immunoassays can employ recombinant antigens which are expressed as a fusion protein by a vector in which the antigen is encoded with the superoxide dismutase (SOD) gene or the CKS (CTP:CMP-3-deoxy--manno-octulosonate cytidylyl transferase or CMP-KDO synthetase) gene (see, U.S. Pat. No. 5,124,255, issued Jun. 23, 1992, which is incorporated herein by reference and U.S. Ser. No. 07/903,043 (now U.S. Pat. No. 5,322,769, issued Jun. 21, 1994), which is incorporated herein by reference). Therefore, those assays which utilize recombinant antigen expressed as fusion proteins with bactia enzymes can exhibit an interfering reaction with anti-SOD or anti-CKS antibodies in patient samples. The effect of this anti-CKS or anti-SOD is not removable as a false positive reaction unless the bacterial enzyme which is employed is denatured prior to its addition in the specimen diluent The bacterial enzyme, preferably recombinandy engineered, can be added to the diluent in concentrations ranging from about 0.001 g/L to about 1 g/L, more preferably from about 0.005 g/L to about 0.5 g/L, and most preferably from about 0.01 g/L to about 0.1 g/L. The bacterial enzyme can be added as a purified or partially purified protein from a bacterial extract. However, it has been discovered that the bacterial enzyme must be denatured prior to addition and use in the diluent.

Denaturation can be effected by methods known in the art, including heating at approximately 50° C. to 60° C. for approximately 20 to 60 minutes, and treatment of the bacterial enzyme with chemicals, such as, 8M urea, guanidine, and some organic solvents.

In accordance with the present invention, a "diluent" is defined herein as an aqueous solution of buffer(s) and salt(s) as well understood in the art and illustrated infra. A preferred buffer is Tris[hydroxymethyl]aminomedane, commercially available under the trade designation TRIS from SIGMA Chemical Co., St. Louis, Mo., or phosphate buffers; suitable buffers include, but are not limited to, buffers such as HEPES (N-[2-hydroxyethyl]piperazine-N'-[2-ethanesulfonic acid]), PIPES (piperazine-N,N'-bis[2-ethanesulfonic acid]), CAPS (3-[cyclohexylamino]-1-propanesulfonic acid) and MOPES (3-[N-morpholino] propanesulfonic acid). Suitable salts include sodium chloride (NaCl) and salts such as phosphate salts and sulfate salts.

In addition, various animal sera, detergents, blocking agents and other components can be added to improve specificity. For example, animal serum proteins such as bovine serum, bovine serum albumin (BSA), fetal calf serum and goat serum can be added in concentrations ranging from about 0.5% v/v to about 50% v/v. Biological detergents such as polyoxyethylenesorbitan, commercially available as Tween® 20, polyoxyethylene ether, commercially available as Triton® X-100, Nonidet P40 (an octylphenol-ethylene oxide condensate), sodium dodecyl sulfate (SDS) or N-lauroylecosine (N-dodecanoyl-N-methylglycine) can be added in concentrations ranging from about 0.01% v/v to about 5% v/v. Chelators such as ethylenediaminetetraacetic acid (EDTA) and ethylene glycol-bis (β-aminoethylether) N,N,N',N'-tetraacetic acid (EGTA) can be added in concentrations ranging from about 2 mM to about 20 mM.

In order to neutralize nonspecific reactions due to other proteins contained in the viral lysates or recombinant proteins that comprise the antigen solutions employed on the solid support, a lymphocyte lysate solution, for example, human T-lymphocyte solution or a host cell lysate solution such as an *E. coli* lysate solution, can be added in concentrations typically ranging from about 0.01% v/v to about 10% v/v. Preservatives such as sodium azide can also be added.

The specimen diluent can be used to dilute test specimens in various assay formats. It is contemplated that the diluent reagent employed for the assay can be provided in the form of a kit with one or more containers such as vials or bottles, with each container containing a separate reagent such as a diluent, a monoclonal antibody or combination thereof, or a recombinant protein employed in the assay.

"Solid phases" ("solid supports") which can be used in the assay formats are known to those in the art and include the walls of wells of a reaction tray, test tubes, polystyrene beads, magnetic beads, nitrocellulose strips, membranes, microparticles such as latex particles, and others. The "solid phase" is not critical and can be selected by one skilled in the art. Thus, latex particles, microparticles, magnetic or non-magnetic beads, membranes, plastic tubes, walls of microtiter wells, glass or silicon chips and red blood cells are all suitable examples. Suitable methods for immobilizing peptides on solid phases include ionic, hydrophobic, covalent interactions and the like.

The present invention provides a diluent, test kit and method for increasing specificity in immunoassays which utilize specific binding members. A "specific binding member," as used herein, is a member of a specific binding pair. That is, two different molecules where one of the molecules through chemical or physical means specifically binds to the second molecule. Therefore, in addition to antigen and antibody specific binding pairs of common immunoassays, other specific binding pairs can include biotin and avidin, carbohydrates and lectins, complementary nucledtide sequences, effector and receptor molecules, cofactors and enzymes, enzyme inhibitors and enzymes, and the like. Furthermore, specific binding pairs can include members that are analogs of the original specific binding members, for example, an analyte-analog. Immunoreactive specific binding members include antigens, antigen fragments, antibodies and antibody fragments, both monoclonal and polyclonal, and complexes thereof, including those formed by recombinant DNA molecules. The term "hapten", as used herein, refers to a partial antigen or non-protein binding member which is capable of binding to an antibody, but which is not capable of eliciting antibody formation unless coupled to a carrier protein.

"Analyte," as used herein, is the substance to be detected which may be present in the test sample. The analyte can be any substance for which there exists a naturally occurring specific binding member (such as, an antibody), or for which a specific binding member can be prepared. Thus, an analyte is a substance that can bind to one or more specific binding members in an assay. "Analyte" also includes any antigenic substances, haptens, antibodies, and combinations thereof. As a member of a specific binding pair, the analyte can be detected by means of naturally occurring specific binding partners (pairs) such as the use of intrinsic factor protein as a member of a specific binding pair for the determination of Vitamin $B_{12}$, the use of folate-binding protein to determine folic acid, or the use of a lectin as a member of a specific binding pair for the determination of a carbohydrate. The analyte can include a protein, a peptide, an amino acid, a hormone, a steroid, a vitamin, a drug including those administered for therapeutic purposes as well as those administered for illicit purposes, a bacterium, a virus, and metabolites of or antibodies to any of the above substances. The details for the preparation of such antibodies and the suitability for use as specific binding members are well known to those skilled in the art. Viruses which can be tested include hepatitis-causing viruses (for example, hepatitis A virus, hepatitis B virus, hepatitis C virus, hepatitis delta, and hepatitis E virus), human immunodeficiency viruses (such as HIV-1, HIV-2), the HTLV-I and HTLV-II viruses, and the like.

"Indicator Reagents" may be used in the various assay formats discussed herein. The "indicator reagent" comprises a "signal generating compound" (label) which is capable of generating a measurable signal detectable by external means conjugated (attached) to a specific binding member for the analyte. "Specific binding member" as used herein means a member of a specific binding pair. That is, two different molecules where one of the molecules through chemical or physical means specifically binds to the second molecule. In addition to being an antibody member of a specific binding pair for the analyte, the indicator reagent also can be a member of any specific binding pair, including either hapten-anti-hapten systems such as biotin or anti-biotin, avidin or biotin, a carbohydrate or a lectin, a complementary nucleotide sequence, an effector or a receptor molecule, an enzyme cofactor and an enzyme, an enzyme inhibitor or an enzyme, and the like. An immunoreactive specific binding member can be an antibody, an antigen, or an antibody/antigen complex that is capable of binding either to the analyte as in a sandwich assay, to the capture reagent as in a competitive assay, or to the ancillary specific binding member as in an indirect assay.

The various "signal generating compounds" (labels) contemplated include chromogens, catalysts such as enzymes, luminescent compounds such as fluorescein and rhodamine, chemiluminescent compounds, radioactive elements, and direct visual labels. Examples of enzymes include alkaline phosphatase, horseradish peroxidase, beta-galactosidase, and the like. The selection of a particular label is not critical, but it will be capable of producing a signal either by itself or in conjunction with one or more additional substances.

The term "test sample" includes biological samples which can be tested by the methods of the present invention described herein and include human and animal body fluids such as whole blood, serum, plasma, cerebrospinal fluid, urine, lymph fluids, and various external secretions of the respiratory, intestinal and genitourinary tracts, tears, saliva, milk, white blood cells, myelomas and the like, biological fluids such as cell culture supernatants, fixed tissue specimens and fixed cell specimens. Any substance which can be diluted and tested with recombinant proteins and assay formats described in the present invention are contemplated to be within the scope of the present invention.

It is contemplated that whatever assay format is chosen will utilize a diluted test sample. Numerous assay formats are known in the art, and all are considered to be within the scope of the invention if recombinant antigens are utilized as capture or indicator reagents in them. Thus, one and two-step sandwich immunoassay, hemagglutination assays, competitive assays, neutralization assays, immunodot assays, are all considered within the scope of the present invention.

The use of haptens is known in the art. It is contemplated that haptens also can be used in assays employing fusion proteins in order to enhance performance of the assay.

The following examples are meant to illustrate, but not to limit, the spirit and scope of the invention.

EXAMPLES

Example 1

Preparation of Recombinant CKS-rp 36 for HIV Assay

A. Preparation of Anion-Exchange Resin. A PD-10 column (available from Pharmacia) was equilibrated with 10 mM phosphate buffer containing 8M urea (pH 7.5). CKS-rp 36 antigen in 6M Guanidine-HCl solution was treated with this column and 10 mM phosphate buffer containing 8M urea (pH 7.5), resulting in CKS-rp 36 antigen in 8M urea solution. It was found that a dialysis method also can be used instead of this solution exchange method. Such processing resulted in a purified and denatured bacterial enzyme preparation.

Then, DEAE ion-exchange resin or a QAE ion-exchange resin was filled up in the column, e.g., DEAE-5PW (available from Toso), Resource-Q (available from Pharmacia), was equilibrated with the 10 mM phosphate buffer containing 8M urea (pH 7.5). Next, CKS-rp 36 antigen in 8M urea solution was passed over the above anion-exchange resin column. CKS-rp 36 antigen was passed by this step at a flow rate of 1 ml/min. The resultant CKS-rp 36 antigen was used in a passive hemagglutation assay (PHA) as an antigen, as follows. The denatured CKS-rp 36 antigen was coated onto human red blood cells type O and used in the PHA assay kit (available from Dainabot, Tokyo, Japan). Three thousand (3,000) volunteer serum donors were tested using this PHA test kit in which the test serum was diluted at the various concentrations noted. The results obtained are summarized in the following Table 1.

TABLE 1

| Number of False Reactions Caused by E. Coli | | | |
| --- | --- | --- | --- |
| | 1:8 | 1:16 | >1:32 |
| Untreated | 1 | 3 | 56 |
| DEAE-Treated | 1 | 2 | 0 |

B. Preparation of Cation-Exchange Resin. A PD-10 column (available from Pharmacia) was equilibrated with 10 mM phosphate buffer containing 8M urea (pH 7.5). CKS-rp 36 antigen in 6M Guanidine-HCl solution was treated with this column and 10 mM phosphate buffer containing 8M urea (pH 7.5), resulting in CKS-rp 36 antigen in 8M urea solution being obtained. It was found that a dialysis method also can be used as the solution exchange method.

Then, CM ion-exchange resin or SP ion-exchange resin was filled up in columns, e.g., CM-3WS (available from Toso), Resource-S (available from Pharmacia) and equilibrated with the 10 mM phosphate buffer containing 8M urea (pH 7.5). Next, CKS-rp 36 antigen was passed over the above cation exchange resin column. The column then was extensively washed, and the CKS-rp 36 antigen was eluted by step elusion with salt at a flow rate of 1 ml/min. The denatuted CKS fusion protein then was coated onto human red blood cells type O, and used as an antigen in the PHA assay described hereinabove. Three thousand (3000) volunteer serum donors were tested using the PHA kit described hereinabove and wherein the test serum was diluted at various concentrations. The results obtained were as summarized in Table 2.

TABLE 2

Number of False Reactions Caused by E. Coli

|  | 1:8 | 1:16 | >1:32 |
|---|---|---|---|
| Untreated | 1 | 3 | 56 |
| CM-Treated | 4 | 1 | 0 |

C. Preparation for anion- and cation-exchange resins. CKS-rp 36 antigen obtained by both of the above treatments were coated onto human red blood cells type O and tested by the PHA assay described hereinabove. The eight (8) specimens which tested as false positive by the methods described in part (A) and (B) herein were retested using the antigen described herein and wherein the test specimens were diluted at various concentrations. The results obtained are summarized in Table 3

TABLE 3

Number of False Reactions Caused by E. Coli

|  | Number Negative (<1:8) | 1:8 | 1:16 | >1:32 |
|---|---|---|---|---|
| Untreated | 0 | 0 | 0 | 8 |
| DEAE-Treated | 5 | 1 | 2 | 8 |
| CM-Treated | 3 | 4 | 1 | 0 |
| DEAE-CM | 8 | 0 | 0 | 0 |

Example 2

Preparation of HIV-Related Antibody Assay Kit

Human red blood cells type O first were washed with physiological saline, pH 7.0, and then incubated with a solution containing DEAE-CM treated HV CKS-rp 36 antigen. The cells were incubated in the antigen solution for two hours at room temperature and washed in phosphate buffered saline. The antigen coated cell solution consisted of 1.0% (v/v) of the antigen coated cells in physiological saline solution. E. coli XL-1 lysates, E. coli JM 103 lysates and E. coli pTB 210XL-1 lysates, 20 µg/ml recombinant CKS lysates and 20 µg/ml purified recombinant CKS was utillied in the PHA assay described herein when testing 3,000 volunteer serum donors. The results are summarized in Table 4 below.

TABLE 4

| Blocking Agent | Number of False Reactions Caused by CKS |
|---|---|
| Control | 16 |
| E. coli XL-1 lysates | 16 |
| E. coli JM 103 lysates | 16 |
| E. coli pTB 210.XL-1 lysates | 0 |
| Recombinant CKS lysates | 0 |
| Purified Recombinant CKS | 0 |

These data indicate that DEAE and/or CM-treatment of CKS-rp 36 HV antigen can be used to reduce the number of false positive reactions caused by E. coli when the CKS materials used are denatured, as they were in this example and Example 1, with 8M urea.

Example 3

Preparation of Recombinant CKS

A synthetic sequence of the DNA was prepared using the method described in U.S. Pat. No. 5,124,255.

Example 4

Specimen Diluent

The sample diluent comprising 10% (v/v) bovine serum and 20% (v/v) goat serum in 20 mM Tris phosphate buffer containing 0.15% (v/v) Triton X-100, 1% (w/v) BSA, and 500 µg/ml or less recombinant CKS bacterial enzyme (prepared as described in Example 3) was prepared, wherein the recombinant CKS bacterial enzyme was denatured at 50° C. for approximately 30 minutes before adding to the diluent.

Example 5

Specificity Panel Testing for HIV Assay

Experiments were conducted in order to assess false reactions due to CKS and determine if heat treatment of the recombinant bacterial enzyme would reduce false positive reactions. Former data had shown that the addition of CKS lysate to the 2nd generation HIV assay (available from Abbott Laboratories, Abbott Park, Ill.) did not increase specificity in the 2nd generation HIV assay by reducing the number of false positive reactions believed to be occurring. Consequently, experiments were designed to determine whether denaturation of the recombinant CKS bacterial enzyme would improve specificity. A specificity panel consisting of 10 members was selected for testing, along with positive and negative controls. The Abbott 2nd generation HIV assay (available from Abbott Laboratories, Abbott Park, Ill.) was used in the experiment. Specimens were run in duplicate, with controls being run five times each. The comparison was made between the diluent available as the standard assay reagent and a diluent which contained CKS recombinant bacterial enzyme (denatured at 50° C. for 30 minutes), as described in Example 4. Assay protocol followed was as recommended by the manufacturer of the assay, with readings obtained reported as optical density readings (O.D.). The results are summarized in the following Table 5.

TABLE 5

| Sample Tested | O.D. Reading/Standard Reagents | O.D. Reading/Addition of Heat-Treated CKS to Diluent |
|---|---|---|
| Negative Control | 0.129 | 0.074 |
|  | 0.168 | 0.061 |
|  | 0.192 | 0.068 |
|  | 0.132 | 0.064 |
|  | 0.107 | 0.068 |
| Positive Control | 1.052 | 1.211 |
|  | 1.026 | 1.141 |
|  | 1.097 | 1.156 |
|  | 0.939 | 1.176 |
|  | 1.065 | 1.276 |
| Panel Member 1 | 0.187 | 0.077 |
|  | 0.166 | 0.052 |

TABLE 5-continued

| Sample Tested | O.D. Reading/Standard Reagents | O.D. Reading/Addition of Heat-Treated CKS to Diluent |
|---|---|---|
| Panel Member 2 | 0.125 | 0.115 |
| | 0.101 | 0.100 |
| Panel Member 3 | 0.092 | 0.075 |
| | 0.085 | 0.062 |
| Panel Member 4 | 0.107 | 0.032 |
| | 0.079 | 0.027 |
| Panel Member 5 | 0.327 | 0.034 |
| | 0.258 | 0.037 |
| Panel Member 6 | 0.174 | 0.139 |
| | 0.211 | 0.132 |
| Panel Member 7 | 0.397 | 0.031 |
| | 0.353 | 0.031 |
| Panel Member 8 | 0.271 | 0.036 |
| | 0.430 | 0.038 |
| Panel Member 9 | 1.609 | 0.076 |
| | >2.000 | 0.069 |
| Panel Member 10 | 0.221 | 0.232 |
| | 0.209 | 0.215 |

These data demonstrate that several members of the 10-member specificity panel showed significant improvement (>50% OD. reduction) including members 1, 4, 5, 7, 8 and 9. Members 7 and 9 went from a positive test interpretation to a negative test interpretation, with panel member 9 showing the most significant effect.

Example 6

Specificity Panel Testing for HIV 1/HIV 2 Test Pack Assay

Experiments were conducted in order to assess false reactions due to CKS and determine if heat treatment of the recombinant bacterial enzyme would reduce false positive reactions in the Abbott Test Pack HIV1/HV2 Assay. Former data had shown that the addition of CKS lysate to the HIV1/HIV2 Test Pack Assay (available from Abbott Laboratories, Abbott Park, Ill.) did not increase specificity in the HIV assay by reducing the number of false positive reactions believed to be occurring. Consequently, experiments were designed to determine whether denaturation of the recombinant CKS bacterial enzyme would improve specificity. A specificity panel consisting of the same 10 members described in Example 7 was selected for testing, along with positive and negative controls. The Abbott HIV 1/HIV 2 Test Pack assay (available from Abbott Laboratories, Abbott Park, Ill.) was used in the experiment. Specimens including positive and negative controls were run in duplicate, and various concentrations of heat teed CKS recombinant bacterial enzyme were tested (12 $\mu$g/ml, 25 $\mu$g/ml, 50 $\mu$g/ml, 75 $\mu$g/ml and 100 $\mu$g/ml). All heat treatment to denature the CKS bacterial enzyme was performed at 50° C. for 30 minutes. Assay protocol followed was as recommended by the manufacturer of the assay, with readings obtained reported as positive, negative or positive/negative. The data obtained from this experiment were similar to those obtained in Example 5, with an improvement in specificity being demonstrated for the HIV1/HIV2 Test Pack assay when denatured CKS recombinant bacterial enzyme was utilized It was noted that in most instances, 12 $\mu$g/ml was a sufficient concentration for increasing specificity, however, it was noted that for panel member 9, the preferred concentration of denatured CKS recombinant bacterial enzyme was 100 $\mu$g/ml.

What is claimed is:

1. A method for detecting antibodies in a specimen which comprises the steps of:
   a) mixing said specimen with a diluent comprising a recombinant denatured bacterial enzyme, wherein said recombinant denatured bacterial enzyme is CKS; and
   b) contacting said specimen with at least one recombinant antigen, wherein said antigen is expressed as a fusion protein of said antigen and a bacterial enzyme and further wherein said bacterial enzyme is CKS.

2. The method of claim 1, wherein said recombinant denatured bacterial enzyme is purified by passing it through an exchange column.

3. The method of claim 1, wherein the concentration of said recombinant denatured bacterial enzyme is from about 0.001 g/L diluent to about 1.0 g/L diluent.

4. The method of claim 3, wherein the concentration of said recombinant denatured bacterial enzyme is from about 0.01 g/L diluent to about 0.1 g/L diluent.

5. The method of claim 1, wherein said recombinant denatured bacterial enzyme is at a concentration of about 100 $\mu$g/ml.

6. The method of claim 1, wherein said method detects anti-HCV antibodies.

7. The method of claim 1, wherein said method detects anti-HIV antibodies.

8. The method of claim 1, wherein said recombinant denatured bacterial enzyme is denatured by heat.

9. The method of claim 1, wherein said recombinant denatured bacterial enzyme is denatured by urea.

10. A test kit useful for performing an immunoassay which comprises a container containing a denatured recombinant bacterial enzyme, wherein said denatured recombinant bacterial enzyme is CKS.

* * * * *